(12) United States Patent
Ayraud

(10) Patent No.: US 7,891,871 B2
(45) Date of Patent: Feb. 22, 2011

(54) INTRA-ORAL DENTAL-IMAGE SENSOR SYSTEM WITH MULTIPLE LEDS

(75) Inventor: Michel Ayraud, Voreppe (FR)

(73) Assignee: E2V Semiconductors (FR)

(*) Notice: Subject to any disclaimer, the term of this patent is extended or adjusted under 35 U.S.C. 154(b) by 25 days.

(21) Appl. No.: 12/513,712

(22) PCT Filed: Nov. 6, 2007

(86) PCT No.: PCT/EP2007/061913
§ 371 (c)(1),
(2), (4) Date: May 15, 2009

(87) PCT Pub. No.: WO2008/058865
PCT Pub. Date: May 22, 2008

(65) Prior Publication Data
US 2010/0040203 A1   Feb. 18, 2010

(30) Foreign Application Priority Data
Nov. 17, 2006   (FR)   ................... 06 10079

(51) Int. Cl.
  *A61B 6/14*   (2006.01)
(52) U.S. Cl. .......................... 378/191; 378/168
(58) Field of Classification Search ........... 378/102, 378/168, 169, 175, 191
See application file for complete search history.

(56) References Cited

U.S. PATENT DOCUMENTS 5,434,418 A * 7/1995 Schick ............... 250/370.11
5,602,668 A * 2/1997 Kuchta ................ 398/172

FOREIGN PATENT DOCUMENTS

| EP | 1 378 201 | 1/2004 |
| FR | 2 883 719 | 10/2006 |
| WO | WO 2006/103126 | 10/2006 |

* cited by examiner

*Primary Examiner*—Hoon Song
(74) *Attorney, Agent, or Firm*—Lowe Hauptman Ham & Berner, LLP

(57) ABSTRACT

The invention relates to intraoral radiological dental image sensors, i.e. sensors placed in the mouth of a patient, an X-ray source being located outside the cheek of the patient in order to emit X-rays in the direction of the sensor. According to the invention, the image sensor is attached to a first end of a short electrical cable (22) of around 5 to 20 cm, a second end of which leaves the patient's mouth when the sensor is in the mouth, the second end carrying a light source (24) comprising light-emitting diodes that can be digitally modulated as a function of information coming from the sensor, the electrical cable being able to transmit an electrical control signal from the sensor to the diode for modulating the latter.

14 Claims, 3 Drawing Sheets

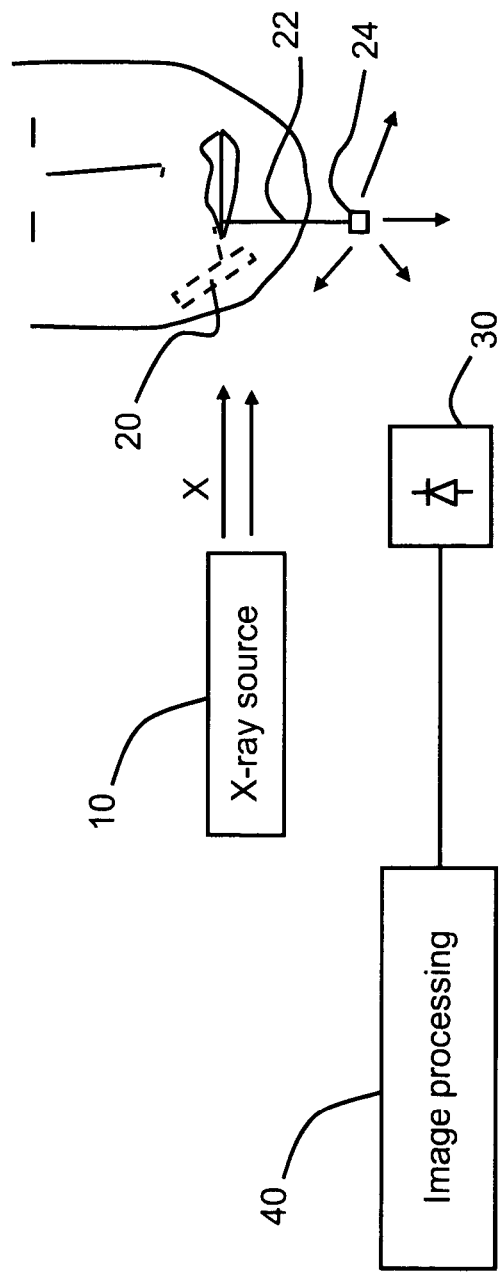
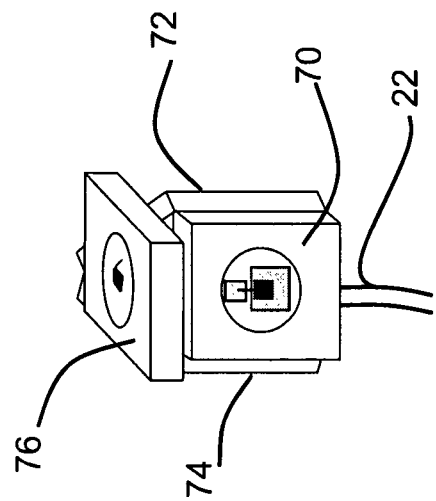

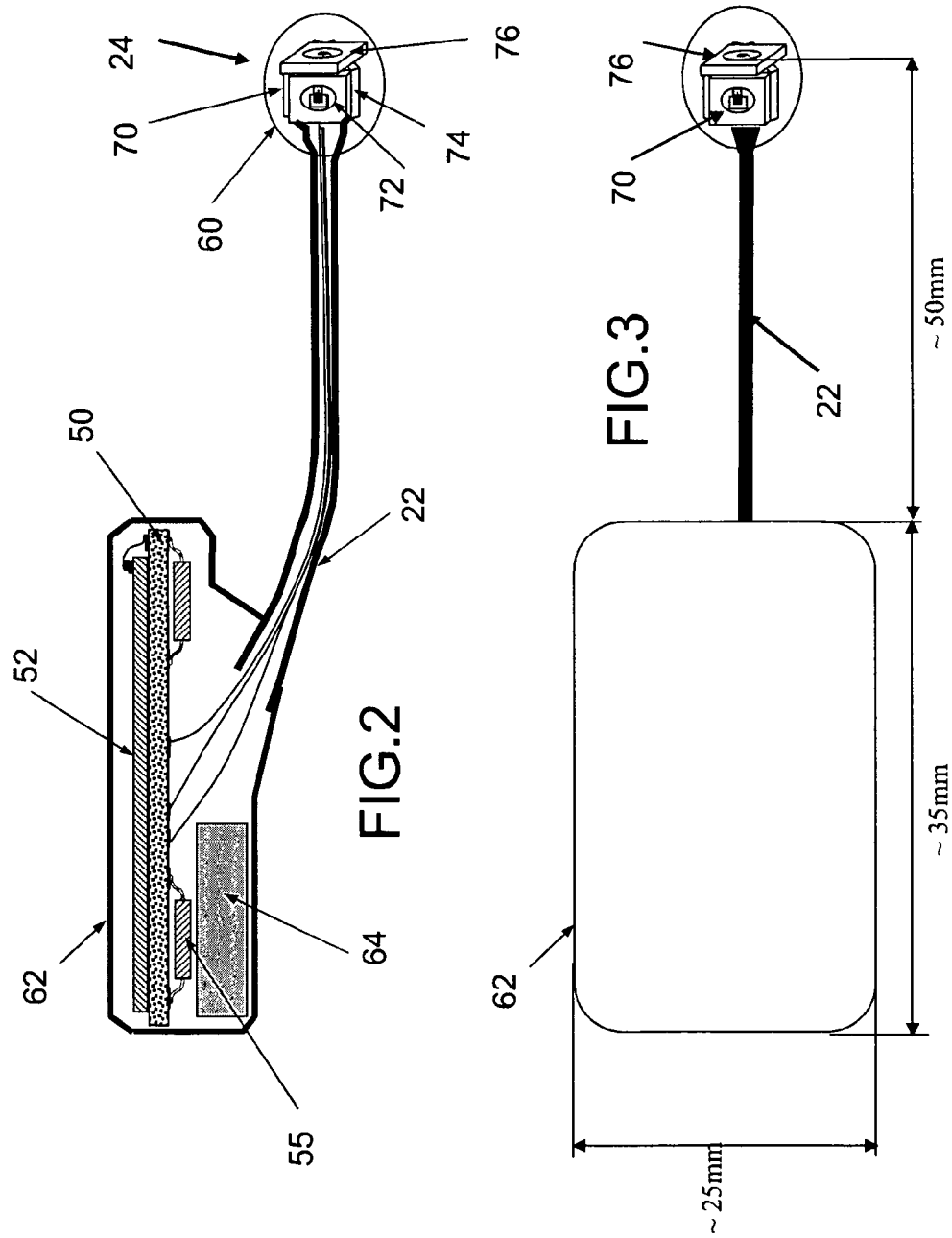

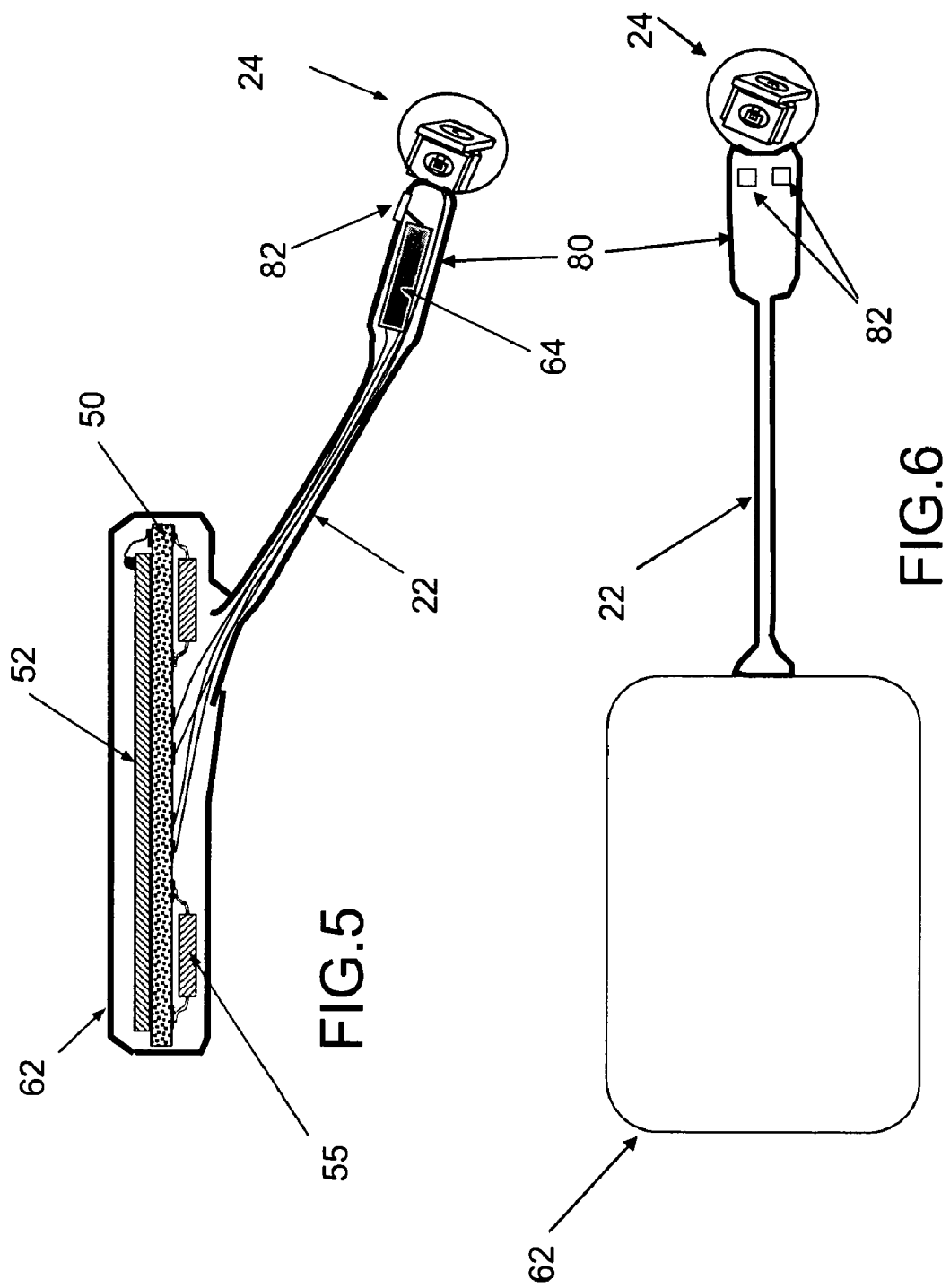

INTRA-ORAL DENTAL-IMAGE SENSOR SYSTEM WITH MULTIPLE LEDS

CROSS-REFERENCE TO RELATED APPLICATIONS

The present Application is based on International Application No. PCT/EP2007/061913, filed on Nov. 6, 2007, which in turn corresponds to French Application No. 0610079, filed on Nov. 17, 2006, and priority is hereby claimed under 35 USC §119 based on these applications. Each of these applications are hereby incorporated by reference in their entirety into the present application.

FIELD OF THE INVENTION

The invention relates to dental radiological systems using an intraoral image sensor, i.e. a sensor placed in the mouth of a patient, an X-ray source being located outside the cheek of the patient in order to emit X-rays in the direction of the sensor.

BACKGROUND OF THE INVENTION

Usually, in order to transmit the image information coming from the sensor placed inside the mouth to a receiver system, a cable connection that is also used to control the sensor and supply it with energy.

The drawback of a cable connection is that it is fragile (risk of being pulled out), inconvenient for the patient if the cable is accidently pulled, and bulky in the overall installation. In addition, in the medical environment the constraints of electrical insulation between the patient and the surrounding electrical power supplies are heightened and it is hardly in accordance with these constraints to connect a mains-powered device (microcomputer) to a module that is in the patient's mouth.

It has therefore been attempted to produce wireless connections both for providing energy and for conveying the information coming from the sensor or toward the sensor. As wireless energy supply (typically by inductive transmission) is not very convenient, it is generally preferred to use a small-sized battery in the sensor placed in the mouth. Furthermore, the image information coming from the sensor must be transmitted at a high data rate (of around 20 megabits per second), and this is why radiofrequency transmissions are preferred, preferably in the unlicensed frequency bands, which are in practice those which are used for wireless communication of information in local networks (frequencies allocated to WLAN networks: 2.45 GHz for example).

However, the difficulty arises in that this radio transmission may then be strongly interfered with through the presence of other radio transmitters which are being used increasingly in IT environments; WiFi or Bluetooth peripherals and computer cards may in particular strongly interfere with the transmission of image data from the sensor to the image user system.

This difficulty can be reduced by emitting the messages in a redundant manner in order to ensure complete and reliable transmission of every image, but this is time consuming when the information to be transmitted is already of a large quantity (typically several tens of megabits per image).

It is also possible to use an "smart" transmitter which examines which frequencies are not used locally in the environment and which adapts its own frequency and/or its own data rate depending on this environment. Such a transmitter necessarily also comprises a receiver. The complex electronics for reception, analysis and intelligent processing that results from this makes it very difficult to put the assembly into the patient's mouth. The bulk and the power consumption are prohibitive. It is therefore necessary to divide the system into a sensor situated inside the mouth, a connecting cable starting from the sensor and which comes out the mouth, a transmitter-receiver in a pocket of the patient, and an intelligent radiofrequency connection between this extraoral transmitter-receiver and the user system (microcomputer) which must collect the images. Such an installation is complex.

Furthermore, in the patent application FR 2 883 719, an intraoral dental sensor is described which provides information to the user system (a personal computer for example) by wireless optical means, in the form of a modulation of the light emitted by a source. The sensor comprises a light source placed on the sensor, and therefore in the mouth, and an optical fiber connected inside the mouth to this source to receive from it light modulated by the sensor. The fiber leaves the mouth and has a free end through which it emits light and the light is received by a receiver connected to the user system. The free end of the fiber is provided with a light diffuser (a small ball of translucent material) which enables approximately omnidirectional light emission.

However, the efficiency of the light transmission toward the receiver is not optimum.

SUMMARY OF THE INVENTION

According to the invention, it is proposed to locate the light source, consisting of at least one light-emitting diode, outside and not inside the patient's mouth. It is then connected to the sensor by an electrical cable which replaces the optical fiber mentioned above, this cable supplying in electrical form the modulation of information produced by the sensor.

The invention therefore proposes an intraoral dental radiological system comprising a radiological image sensor capable of being inserted into the patient's mouth, the sensor comprising an image sensor array providing electronic signals representing a radiological image, an electrical cable having a first end connected to the radiological image sensor and a second end leaving the mouth when the image sensor is in the mouth, the second end having a light source that can be digitally modulated as a function of electrical information coming from the sensor, and a light receiver located at a distance from the patient which is able to detect a modulation of the light emitted by the source, and able to transmit a signal corresponding to this modulation to an image processing device.

Thus, in operation, the light emitter is not situated in the mouth but outside the mouth, and it is in electrical form that the modulation is transmitted from the sensor array located in the mouth to the source placed outside the mouth.

Preferably, the diode is not a single diode; rather, there are at least four light-emitting diodes which have receive the modulation produced by the sensor in parallel and which have different physical orientations so as to emit in a wide range of directions. The aim is not to have to worry about the orientation of the light source in relation to the light receiver.

If there are exactly four diodes, the preferred respective orientation is the following: three diodes emit along three main illumination lobes, the central directions of which are at 120° to each other in the same plane, and a fourth diode emits along an illumination lobe, the central direction of which is perpendicular to this plane. In practice, each light-emitting diode consists of an integrated circuit chip mounted on a planar substrate and the illumination lobe is roughly centered about a main emission direction perpendicular to this substrate. It is therefore the substrates that are juxtaposed, three of them being situated in planes at 120° to each other, and the fourth being in a plane perpendicular to the three others. The electrical cable which provides the electrical modulation to the diodes then arrives in principle through the rear of the substrates, passing inside the triangular-based cylinder formed by the first three substrates, which cylinder is closed by the fourth substrate and which is open opposite the fourth substrate.

It will be understood that it would be possible to use five diodes, on substrates that are at 90° to each other, four substrates forming a square-based cylinder and the fifth closing this cylinder on one side. A number of light-emitting diodes greater than 5 is even conceivable to increase further the omnidirectional character of the emission.

Whatever the number of light-emitting diodes used, according to the invention it is preferred for the self-contained electrical power-supply of the intraoral sensor (primary cell or rechargeable battery) to be placed not inside but outside the mouth, the electrical cable being used to transmit power-supply energy from the source outside the mouth to the sensor inside the mouth. This makes it possible notably to reduce the bulk and the weight of the intraoral sensor, and that makes it possible to use a rechargeable battery rather than a primary cell. The advantage of a rechargeable battery over a primary cell is that a primary cell would often need to be changed. The rechargeable battery has the disadvantage of being more bulky, but the bulk is much less inconvenient once it is located outside the mouth. The electrical connection through the cable makes it possible to position the battery outside the mouth, the cable being used not only to transmit image information from the sensor array toward the light-emitting diodes, but also to transmit to the sensor array the energy necessary for its operation.

The light-emitting diodes may also be used as a receiver of modulated light which would be emitted by the system. This is advantageous notably for transmitting instructions from the system to the intraoral sensor (for example, instructions to transmit an image or to repeat a transmission, or an acknowledgement of transmission, or alternatively a synchronization signal for synchronizing the recording of an image with the emission of an X-ray flash by the system).

The invention relates not only to the system thus defined, but also to the intraoral sensor itself, comprising a radiological image sensor array to be inserted into the mouth, attached to a short electrical cable designed to leave the mouth when the array is in the mouth, the cable having at its end a light source that can be digitally modulated by electrical information coming from the array and transmitted by the electrical cable. A short electrical cable is understood to mean a cable of a few centimeters to several tens of centimeters in length (in practice around 5 cm to around 20 cm).

Still other objects and advantages of the present invention will become readily apparent to those skilled in the art from the following detailed description, wherein the preferred embodiments of the invention are shown and described, simply by way of illustration of the best mode contemplated of carrying out the invention. As will be realized, the invention is capable of other and different embodiments, and its several details are capable of modifications in various obvious aspects, all without departing from the invention. Accordingly, the drawings and description thereof are to be regarded as illustrative in nature, and not as restrictive.

BRIEF DESCRIPTION OF THE DRAWINGS

The present invention is illustrated by way of example, and not by limitation, in the figures of the accompanying drawings, wherein elements having the same reference numeral designations represent like elements throughout and wherein:

FIG. 1 shows a dental radiological system according to the invention;

FIG. 2 shows a sectional view of a practical embodiment of the image sensor;

FIG. 3 shows a view of the sensor from above;

FIG. 4 shows the detail of the four light-emitting diodes; and

FIGS. 5 and 6 show a modification in which the battery is placed at the outside end of the cable.

DETAILED DESCRIPTION OF THE INVENTION

FIG. 1 shows the dental radiological system according to the invention in schematic form: it comprises an X-ray source 10 capable of emitting an X-ray flash toward the part of the jaw to be examined, a radiological image sensor 20 placed in the patient's mouth and shown in dotted lines, a photosensitive receiver 30 located outside the patient's mouth but not electrically connected to the sensor, and a system for using the signal received by the receiver. This user system 40 is designated in FIG. 1 as the image processing system, image processing being taken in the broad sense and possibly including, for example, receiving and demodulating digital light signals detected by the receiver, in order to extract from them image information which they are carrying and in order to transform the demodulated signals into an electronic image. This image is intended to be stored in a memory of the system or displayed on a display screen (not shown).

The core of the radiological image sensor is a radiological image sensor array which conventionally comprises a scintillator layer, sensitive to X-rays and converting the received X-ray image into a light image, and a light image sensor array placed behind the scintillator layer. The radiological image sensor array provides digital electronic signals (or analog signals, but then converted into digital signals) representing the radiological image captured at the moment of the X-ray flash.

The image sensor array 20 is electrically connected by a cable 22 to a light-emitting source 24. The cable 22 transmits an electrical modulation to this source corresponding to the digital electronic signals coming from the array and representing the radiological image. The light source 24 preferably consists of a set of several light-emitting diodes receiving the same modulation and emitting along radiation lobes with different orientations so that the emission is as omnidirectional as possible.

The photosensitive receiver 30 collects the light, converts it into electronic signals and transmits it to the user system 40. The receiver is preferably provided with a wavelength selection filter centered on the main wavelength emitted by the light source so that other light sources present in the environment interfere with reception as little as possible. The pass-band of the filter may be around 30 nanometers. The receiver may be located quite close to the patient, for example a few tens of centimeters away or less. Specifically, it may be held by a part of the system that also holds the X-ray source. It is known that the X-ray source is generally located on an articulated arm which enables it to be moved up to a few centimeters from the cheek. The receiver may be held by the same articulated arm.

In FIG. 2 the detail of an intraoral sensor according to the invention can be seen.

The sensor comprises a printed circuit 50 carrying, on one face, an integrated circuit chip 52, on one face of which the actual radiological image sensor is formed, namely a light image sensor array coated with a scintillator reacting to X-rays. The array generates electronic signals representing the light levels of points of the image. The chip 52, a few centimeters on a side, comprises the analog-digital conversion circuits for converting the electronic image into digital signals representing each pixel.

The electrical cable 22 sends these signals to the light source 24. The length of the cable may be from a few centimeters to a few tens of centimeters. A value of around 3 cm to 20 cm is preferred for the part of the cable that leaves the mouth when the sensor is in place.

The light emitted is preferably an infrared light at an eye-safe wavelength and preferably quite strongly monochromatic. The printed circuit 52 may comprise other circuitry elements such as the component 55 represented in FIG. 2.

The whole of the printed circuit 50 and its components, with the integrated circuit chip 52 and the first end of the electrical cable 22, is housed in a sealed case 62 from which the cable issues. The case may optionally contain a primary cell or a rechargeable battery 64 enabling self-contained electrical power-supply of the printed circuit and components it bears.

In one exemplary embodiment, the dimensions of the sensor case are the following: L=around 35 mm, I=around 25 mm, H=around 10 mm. FIG. 3 shows a view of the sensor from above.

In the exemplary embodiment shown in FIGS. 2 and 3 the light source 24 consists of an assembly of four light-emitting diodes (or LEDs) 70, 72, 74, 76 receiving the same electrical modulation coming from the sensor. The diodes are arranged in relation to each other such that the assembly emits light according to a ray diagram that is as omnidirectional as possible. This makes it possible not to worry about the position and the precise orientation of the source relative to the receiver. The latter will in practice always receive a sufficient amount of light, given that the modulation is digital and that digital information can be detected even with a relatively low signal-to-noise ratio.

The preferred arrangement, which combines good omni-directionality and easy assembly of the four light-emitting diodes, is the following: the diodes emit along a main radiation lobe, the axis of which is perpendicular to the plane of the substrate on which they are arranged. Three substrates 70, 72, 74 are arranged in planes at 120° to each other and oriented such that the diodes emit outward from the trihedron formed by the three substrates. The three planes are parallel to a single axis, and the fourth substrate 76 is perpendicular to this axis and it emits outward from the case formed by the four substrates. The electrical cable arrives inside this case, at the rear of the substrates of the diodes.

The four diodes and their substrates, along with the second end of the electrical cable 22, are embedded in a transparent protective plastic 60.

FIG. 4 shows the detail of assembly of the four light-emitting diodes.

Another advantageous solution consists in using five diodes. In this case there will be four diodes on four substrates at 90° to each other (forming a square-based cylinder) open on one side for receiving the cable and closed on the other by the substrate of the fifth diode, also at 90° to the others but perpendicular to the axis of the cylinder defined by the first four.

In a particularly advantageous variant embodiment shown in FIGS. 5 and 6, provision is made for the primary cell or rechargeable battery 64, which is used as the electrical power-supply of the array 52 placed in the patient's mouth, to be located at the end of the electrical cable 22, i.e. outside the patient's mouth. This reduces the bulk (notably the thickness) and the weight of the intraoral sensor and this makes it possible to use a rechargeable battery rather than a non-rechargeable primary cell.

The primary cell or rechargeable battery 64 may be located in immediate proximity to the light source 24, as is shown in FIGS. 5 and 6, or alternatively in an intermediate position of the cable between the light source and the sensor (but still outside the mouth). The battery is located in a case 80. The cable 22 then comprises not only the electrical wires necessary for the transmission of signals to the diodes, but also the wires necessary for the power supply for the sensor. The battery case may, if the latter is rechargeable, comprise electrodes 82 enabling the connection to an external charger. The battery might also be recharged without contact by an inductive method, a coil and a rectification circuit then being provided inside the case and the recharging being carried out from an inductive transmission charger.

The LEDs receive the digital modulation coming from the sensor which is placed in the mouth. However, it is possible to make provision for a small amplification circuit associated with the LEDs to be located in immediate proximity to the latter, i.e. at the end of the cable 22, for example in a housing reserved for this purpose in the battery case. This circuit is supplied with power directly by the battery 64.

Optionally, it is possible to make provision for the radiological system also to comprise means for optical communication in the reverse direction, namely from the system to the sensor placed in the mouth. A light emitter associated with the system may emit light pulses conveying information or instructions, the wavelength of the light emitted for this purpose preferably being different to the wavelength emitted by the light-emitting diodes so that there is no detrimental interference between the outgoing light pulses and the returning light pulses. The pulses emitted by the system to the sensor may be detected by a photodiode (not shown).

It is also possible to make provision for the light-emitting diodes themselves to serve as detectors for gathering these pulses coming from the system. It is then necessary to provide a control circuit for the light-emitting diodes which is able to make them work either as light emitters or as light detectors. Emission and reception do not take place at the same time and it is therefore necessary to provide switches for connecting the diodes either in an emission circuit or in a reception circuit depending on the time.

By way of example, the return pulses (from the system toward the sensor) may be used to send a piece of information for triggering an X-ray flash, or to request the sensor to send or resend an image or a part of an image, or alternatively to parameterize some functions of the sensor (exposure time, etc.). The information data rate in the return direction may be much lower than in the outward direction as there is no image to be transmitted.

There may be several receivers, such as the receiver 30, around the patient, so as to increase the probability of correct reception of the transmitted image. It is possible, for example, to make provision for the receiver system to process the signals received from the various receivers separately, to determine the error rate of each and to choose the receiver that offers the lowest error rate in order to continue reception with the latter.

It will be readily seen by one of ordinary skill in the art that the present invention fulfils all of the objects set forth above. After reading the foregoing specification, one of ordinary skill in the art will be able to affect various changes, substitutions of equivalents and various aspects of the invention as broadly disclosed herein. It is therefore intended that the protection granted hereon be limited only by definition contained in the appended claims and equivalents thereof.

The invention claimed is:

1. An intraoral dental radiological system comprising
a radiological image sensor adapted for being inserted into a patient's mouth, the sensor comprising an image sensor array providing electronic signals representing a radiological image,
an electrical cable having a first end connected to the radiological image sensor and a second end located outside of the mouth when the image sensor is in the mouth, the second end having a light source that is digitally modulated as a function of electrical information coming from the sensor, and
a light receiver located at a distance from the patient for detecting a modulation of the light emitted by the source and transmitting a signal corresponding to the modulation to a device for exploiting the signal,
wherein the light source comprises at least four light-emitting diodes which receive the modulation produced by the sensor in parallel and which have different physical orientations so as to emit in a wide range of directions.

2. The radiological system as claimed in claim 1, wherein three diodes emit along three main illumination lobes, the axes of which are at 120° to each other in the same plane, and a fourth diode emits along an illumination lobe, the axis of which is perpendicular to this plane.

3. The radiological system as claimed in claim 2, wherein each light-emitting diode consists of an integrated circuit chip mounted on a planar substrate and the axis of the illumination lobe considered for a given chip is perpendicular to this substrate, the substrates are juxtaposed, three of them being situated in planes at 120° to each other, and the fourth being in a plane perpendicular to the three others.

4. The radiological system as claimed in claim 2, wherein a self-contained electrical power-supply of the intraoral sensor is placed on the electrical cable, outside the mouth when the sensor is in the mouth, the electrical cable also being used to transmit power-supply energy from the source outside the mouth to the sensor inside the mouth.

5. The radiological system as claimed in claim 1, wherein the light source comprises five diodes on substrates that are at 90° to each other, four substrates forming a square-based cylinder and the fifth closing this cylinder on one side.

6. The radiological system as claimed in claim 1, wherein a self-contained electrical power-supply of the intraoral sensor is placed on the electrical cable, outside the mouth when the sensor is in the mouth, the electrical cable also being used to transmit power-supply energy from the source outside the mouth to the sensor inside the mouth.

7. An intraoral dental radiological system comprising
a radiological image sensor adapted for being inserted into a patient's mouth, the sensor comprising an image sensor array providing electronic signals representing a radiological image,
an electrical cable having a first end connected to the radiological image sensor and a second end located outside of the mouth when the image sensor is in the mouth, the second end having a light source that is digitally modulated as a function of electrical information coming from the sensor, and
a light receiver located at a distance from the patient for detecting a modulation of the light emitted by the source and transmitting a signal corresponding to the modulation to a device for exploiting the signal,
wherein a self-contained electrical power-supply of the intraoral sensor is placed on the electrical cable, outside the mouth when the sensor is in the mouth, the electrical cable also being used to transmit power-supply energy from the source outside the mouth to the sensor inside the mouth.

8. The radiological system as claimed in claim 7, wherein the light-emitting diodes are also used as a receiver of modulated light emitted by the system.

9. An intraoral image sensor comprising
a radiological image sensor array for providing electronic signals representing a radiological image, said sensory array attached to a first end of a short electrical cable of around 5 to 20 cm, a second end of which leaves the mouth of a patient when the array is in the mouth, the cable being terminated at the second end by a light source that is digitally modulated as a function of electrical information coming from the sensor array and transmitted by the cable,
wherein the light source comprises at least four light-emitting diodes which receive the modulation produced by the sensor in parallel and which have different physical orientations so as to emit in a wide range of directions.

10. The intraoral image sensor as claimed in claim 9, wherein three diodes emit along three main illumination lobes, the axes of which are at 120° to each other in the same plane, and a fourth diode emits along an illumination lobe, the axis of which is perpendicular to this plane.

11. The intraoral image sensor as claimed in claim 10, wherein each light-emitting diode consists of an integrated circuit chip mounted on a planar substrate and the axis of the illumination lobe considered for a given chip is perpendicular to this substrate, the substrates are juxtaposed, three of them being situated in planes at 120° to each other, and the fourth being in a plane perpendicular to the three others.

12. The intraoral image sensor as claimed in claim 9, wherein the light source comprises five diodes on substrates that are at 90° to each other, four substrates forming a square-based cylinder and the fifth closing this cylinder on one side.

13. The intraoral image sensor as claimed in claim 9, wherein a self-contained electrical power-supply of the intraoral sensor is placed on the electrical cable, outside the mouth when the sensor is in the mouth, the electrical cable also being used to transmit power-supply energy from the source outside the mouth to the sensor inside the mouth.

14. An intraoral image sensor comprising
a radiological image sensor array for providing electronic signals representing a radiological image, said sensory array attached to a first end of a short electrical cable of around 5 to 20 cm, a second end of which leaves the mouth of a patient when the array is in the mouth, the cable being terminated at the second end by a light source that is digitally modulated as a function of electrical information coming from the sensor array and transmitted by the cable,
wherein a self-contained electrical power-supply of the intraoral sensor is placed on the electrical cable, outside the mouth when the sensor is in the mouth, the electrical cable also being used to transmit power-supply energy from the source outside the mouth to the sensor inside the mouth.

* * * * *